US007651222B2

(12) United States Patent
Yang

(10) Patent No.: US 7,651,222 B2
(45) Date of Patent: Jan. 26, 2010

(54) EYE MUSCLE TRAINER

(76) Inventor: David Min-Liang Yang, 2F, No. 5, Alley 9, Lane 123, Sec. 3, Ren-Ai Rd., Da-An Dist., Taipei (TW)

( * ) Notice: Subject to any disclaimer, the term of this patent is extended or adjusted under 35 U.S.C. 154(b) by 0 days.

(21) Appl. No.: 12/153,468

(22) Filed: May 20, 2008

(65) Prior Publication Data

US 2009/0290123 A1 Nov. 26, 2009

(51) Int. Cl.
*A61B 3/00* (2006.01)

(52) U.S. Cl. ....................................... 351/203; 351/245

(58) Field of Classification Search ................. 351/200, 351/202, 203, 222, 237, 243–245
See application file for complete search history.

(56) References Cited

U.S. PATENT DOCUMENTS

| | | | | |
|---|---|---|---|---|
| 3,936,162 | A * | 2/1976 | Krakau et al. | 351/243 |
| 2007/0200927 | A1 * | 8/2007 | Krenik | 348/47 |

* cited by examiner

*Primary Examiner*—Huy K Mai
(74) *Attorney, Agent, or Firm*—Bacon & Thomas, PLLC

(57) ABSTRACT

An eye muscle trainer has an outer casing, a control circuit module, a first light emitting unit set, two second light emitting unit sets, two third light emitting unit sets and an eye frame. The outer casing is opaque and has a rear opening. The light emitting unit sets are mounted on the control circuit module. The first light emitting unit set is for focusing user's vision. The second light emitting unit sets are for focusing user's vision on seeing straightly. The third light emitting units are for focusing the user's vision on seeing outwardly. The eye frame accommodates the rear opening of the outer casing. Therefore, wearing the eye muscle trainer releases eyestrain because watching the light emitting unit sets arranged at different position exercises the user's eyes. Consequently, appropriate releasing eyestrain assists improving eyesight.

9 Claims, 6 Drawing Sheets

EYE MUSCLE TRAINER

BACKGROUND OF THE INVENTION

1. Field of the Invention

The present invention relates to an eye muscle trainer, and more particularly to an eye muscle trainer that exercises muscles around eyes to improve eyesight.

2. Description of Related Art

Eyes are organs for humans seeing things. A movement of each eyeball is controlled by muscles around the eye. Relaxation and tension of the muscles make the eyeball turn, rotate or move. The muscles around each eye comprise a lateral rectus muscle, a medial rectus muscle, an inferior rectus muscle, a superior rectus muscle, an inferior oblique muscle and a superior oblique muscle. When a person looks near sights, the medial rectus muscle and the superior oblique muscle will be tensioned, and the lateral rectus muscle, the inferior rectus muscle, the superior rectus muscle and the inferior oblique muscle will be relaxed. On the contrary, when the person looks far sights, the medial rectus muscle and the superior oblique muscle will be relaxed, and the lateral rectus muscle, the inferior rectus muscle, the superior rectus muscle and the inferior oblique muscle will be tensioned. Furthermore, when the person looks extremely far sights, the medial rectus muscle and the superior oblique muscle will be extremely relaxed, and the lateral rectus muscle, the inferior rectus muscle, the superior rectus muscle and the inferior oblique muscle will be extremely tensioned.

In addition, strabismus may cause lacking of coordination between the eye muscles naturally, pathological changes or any possible reasons. Strabismus may comprise medial strabismus (so-called cross-eye), lateral strabismus, superior strabismus and etc. However, strabismus is not treated as a disease so strabismus is not taken seriously by the medical science. If strabismus is not cured, it is inconvenient for people to see things.

In addition, today's life is busy and stressful so people use their eyes quite a long time everyday. Once the eyes are overused, the muscles around the eyes may lose its elasticity. Fatigued muscles around eyes may cause eyesight problems, such as near-sightedness, far-sightedness or the like. A common treatment for the eye diseases is using eyeglasses. However, eyeglasses only help people to see more clearly and prevent the eyesight from getting worse but not improve the eyesight.

To overcome the shortcomings, the present invention provides an eye muscle trainer that exercises muscles around the eye to improve eyesight to mitigate or obviate the aforementioned problems.

SUMMARY OF THE INVENTION

The main objective of the invention is to provide an eye muscle trainer that exercises muscles around the eye to improve eyesight.

The eye muscle trainer in accordance with the present invention comprises an outer casing, a control circuit module, a first light emitting unit set, two second light emitting unit sets, two third light emitting unit sets and an eye frame. The outer casing is opaque and has a rear opening. The light emitting unit sets are mounted on the control circuit module. The first light emitting unit set is for focusing user's vision. The second light emitting unit sets are for focusing user's vision on seeing straightly. The third light emitting units are for focusing the user's vision on seeing outwardly. The eye frame accommodates the rear opening of the outer casing and is semiopaque. Therefore, wearing the eye muscle trainer releases eyestrain because watching the light emitting unit sets arranged at different position exercises the user's muscles around eyes. Consequently, appropriate releasing eyestrain assists improving eyesight.

Other objectives, advantages and novel features of the invention will become more apparent from the following detailed description when taken in conjunction with the accompanying drawings.

DETAILED DESCRIPTION OF PREFERRED EMBODIMENT

Figure 1:
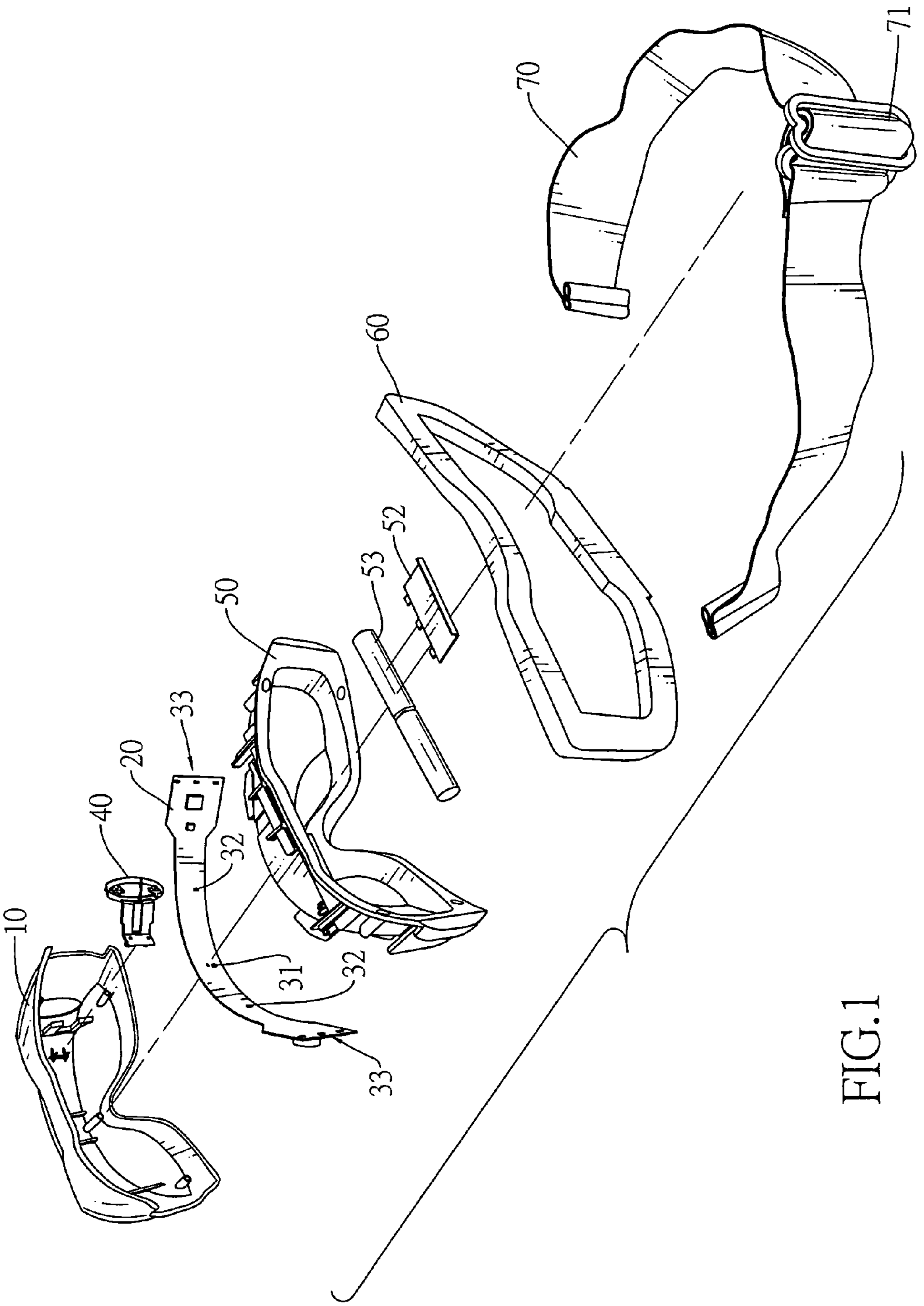
FIG. 1 is an exploded perspective view of an eye muscle trainer in accordance with the present invention.

With reference to FIG. 1, an eye muscle trainer in accordance with the present invention comprises an outer casing (10), at least two light emitting unit sets, an optional switch unit (40), an eye frame (50), an optional rim pad (60) and an optional head belt (70).

The outer casing (10) is opaque and has a rear opening.

The control circuit module (20) is mounted in the outer casing (10). Furthermore, the control circuit module (20) may comprise a center segment and two wing segments, wherein the center segment is connected between the two wing segments.

The at least two light emitting unit sets may comprise a first light emitting unit set (31), a second light emitting unit set (32) and a third light emitting unit set (33). The light emitting unit sets (31, 32, 33) are mounted on the control circuit module (20) and are selectively activated by the control circuit module (20). A distance between a user's eyes and the light emitting unit sets (31, 32, 33) when the user wears the eye muscle trainer is between 5 to 10 centimeters because eyes will not be interfere by other light emitting unit sets when focusing one of the light emitting unit sets. Furthermore, each light emitting unit set (31, 32, 33) comprises at least one light emitting unit. The first light emitting unit set (31) may comprise one light emitting unit and is mounted on the center of the center segment of the control circuit module (20) for focusing the user's vision on the first light emitting unit set (31). The second light emitting unit set (32) may comprise two light emitting units, and the two light emitting units of the second light emitting unit set (32) are arranged horizontally on the center segment of the control circuit module (20) and are separated from each other by the first light emitting unit set (31) with the same distance for focusing the user's vision on seeing straightly. The third light emitting unit set (33) may comprise six light emitting units, and three of the light emitting units and the other three of the light emitting units of the third light emitting unit set (33) are arranged respectively on the wing segments of the control circuit module (20) for focusing the user's vision on seeing outwardly.

Figure 2:
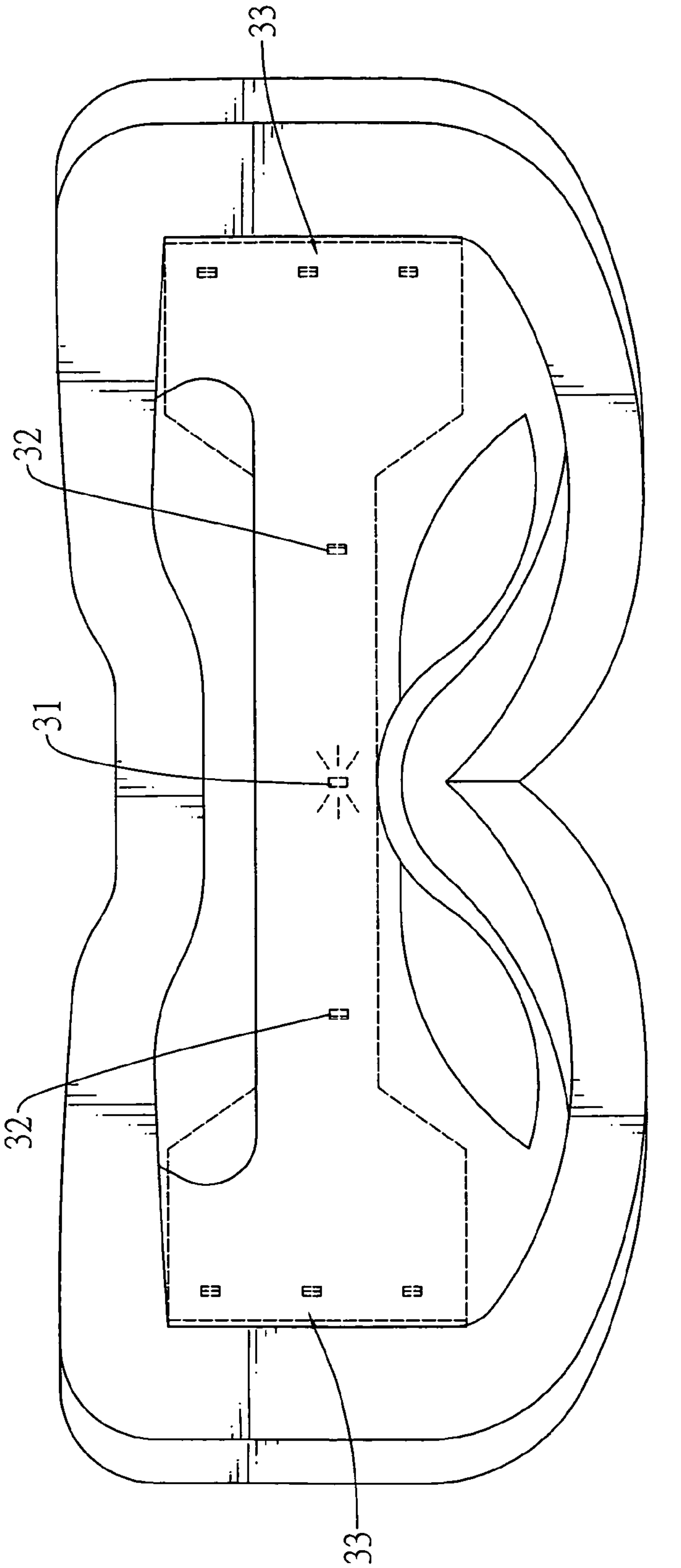
FIG. 2 is a rear view of the eye muscle trainer with a first light emitting unit set generating lights.

With further reference to FIG. 2, when the user is watching the activated first light emitting unit set (31), the user's medial rectus muscles and superior oblique muscles will be tensioned, and the user's lateral rectus muscles, inferior rectus muscles, superior rectus muscles and inferior oblique muscles will be relaxed.

Figure 3:
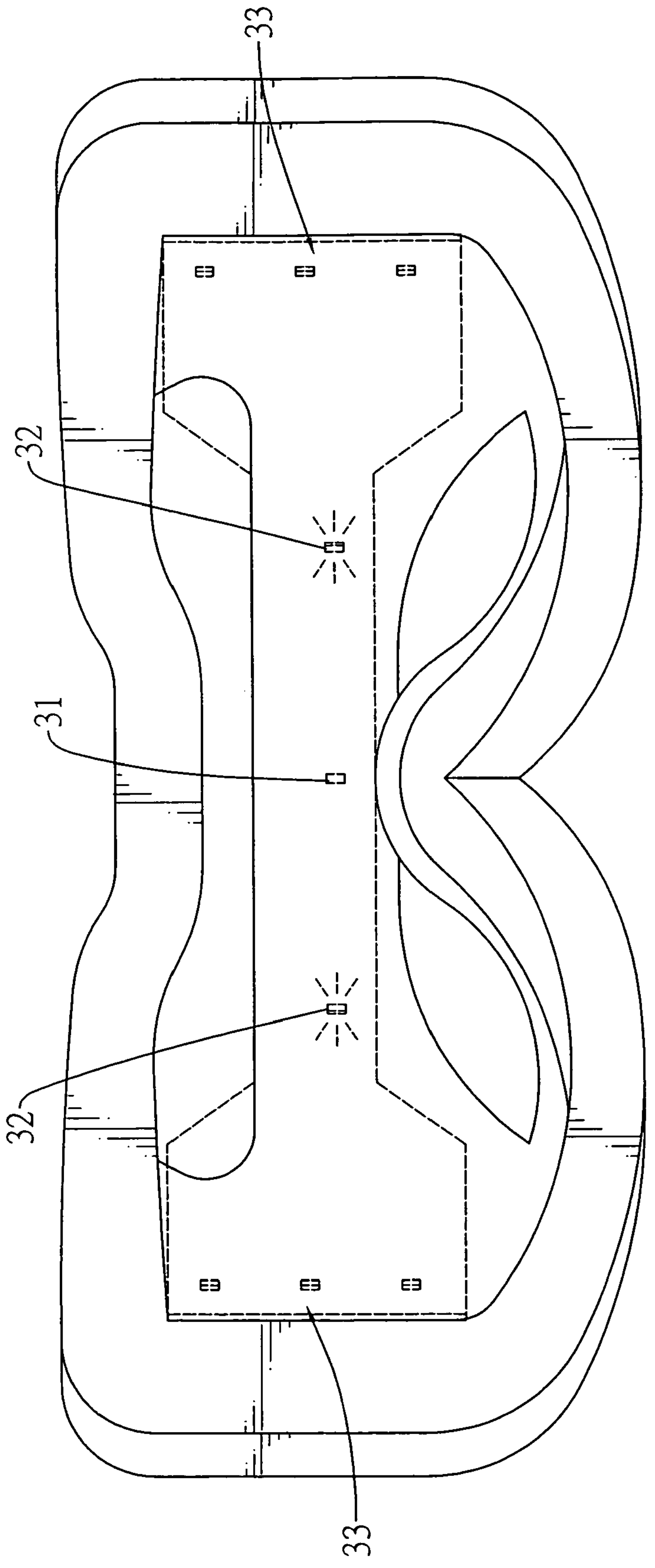
FIG. 3 is a rear view of the eye muscle trainer with two second light emitting unit sets generating lights.

With further reference to FIG. 3, when the user is watching the activated second light emitting unit set (32), the user's medial rectus muscles and superior oblique muscles will be relaxed, and the user's lateral rectus muscles, inferior rectus muscles, superior rectus muscles and inferior oblique muscles will be tensioned.

Figure 4:
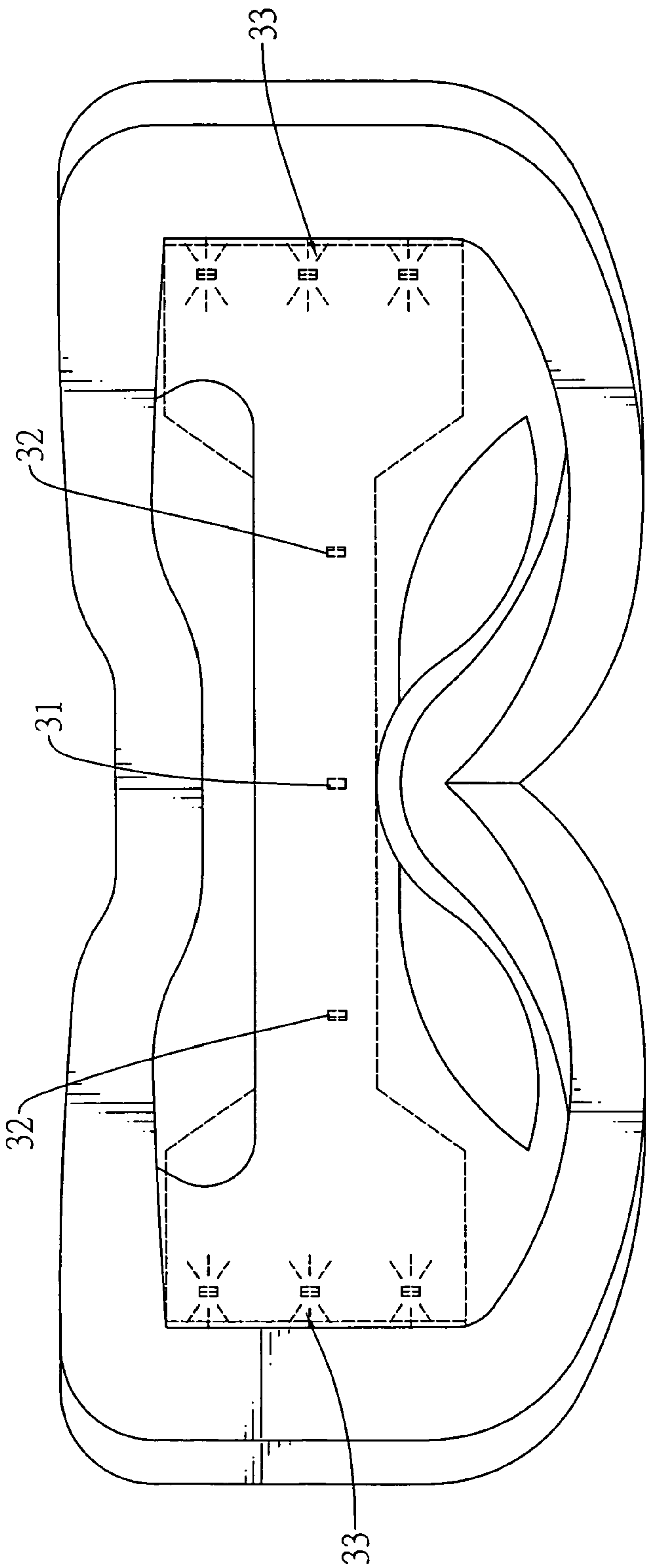
FIG. 4 is a rear view of the eye muscle trainer with two third light emitting unit sets generating lights.

With further reference to FIG. 4, when the user is watching the activated third light emitting unit set (33), the user's medial rectus muscles and superior oblique muscles will be extremely relaxed, and the user's lateral rectus muscles, inferior rectus muscles, superior rectus muscles and inferior oblique muscles will be extremely tensioned.

Furthermore, the control circuit module (20) determines how long the eye muscle trainer operates, how the light emitting units flash in sequence, how the light emitting units flash periodically and how bright the light emitting units generate lights. For example, the control circuit module (20) may control the light emitting units operating as follows:

1. the light emitting units of the third light emitting unit set (33) repeatedly flash in sequence.

2. the first light emitting unit set (31) and the second light emitting unit set (32) flash in sequence.

3. the first light emitting unit set (31), the second light emitting unit set (32) and the third light emitting unit set (33) flash in sequence.

4. the third light emitting unit set (33), the second light emitting unit set (32) and the first light emitting unit set (31) flash in sequence.

5. all light emitting units flash together.

Watching the flashing third light emitting unit set (33) is helpful to relax the user's medial rectus muscles and superior oblique muscles around eyes so as to assist in treating medial strabismus. Watching the first light emitting unit set (31) and the second light emitting unit set (32) being flashing in sequence is helpful to improve the user's eyesight from lateral strabismus. Watching the first light emitting unit set (31), the second light emitting unit set (32) and the third light emitting unit set (33) being flashing in sequence is helpful to improve the user's eyesight from near-sightedness. Watching the third light emitting unit set (33), the second light emitting unit set (32) and the first light emitting unit set (31) being flashing in sequence is helpful to improve the user's eyesight from far-sightedness. Watching all the light emitting units being flashing helps to exercise the user's pupils.

In addition, the control circuit module (20) may control the eye muscle trainer operating for 5, 10 or 15 minutes. The control circuit module (20) may control each light emitting unit flashing per 0.5, 1 or 3 seconds.

Figure 5:
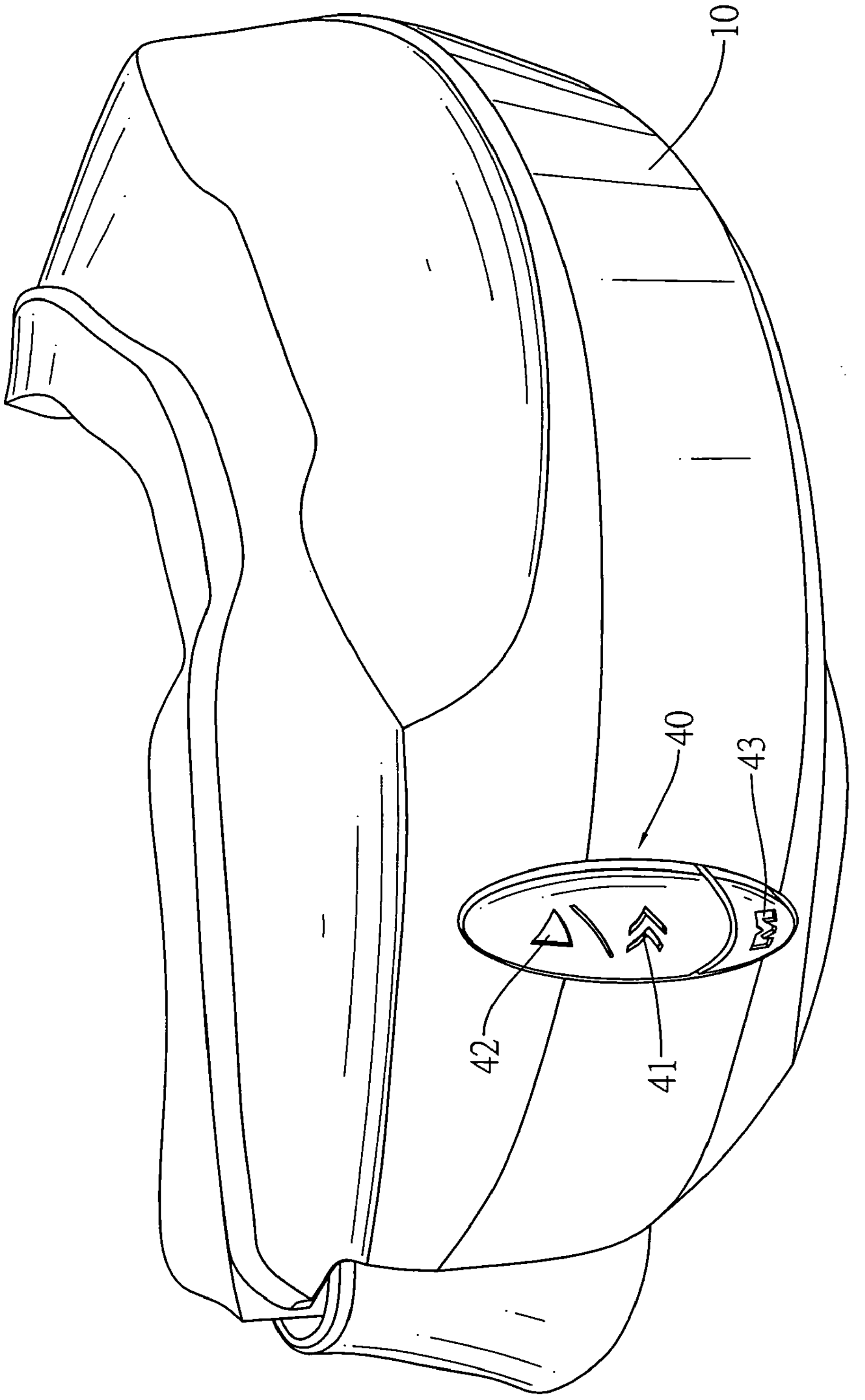
FIG. 5 is a front perspective view of the eye muscle trainer.

With further reference to FIG. 5, the switch unit (40) is mounted in and exposes through the outer casing (10) and is electrically connected to the control circuit module (20) to allow the user to control the eye muscle trainer. Furthermore, the switch unit (40) may comprise an ON switch (41), an OFF switch (42) and a functional key (43).

Figure 6:
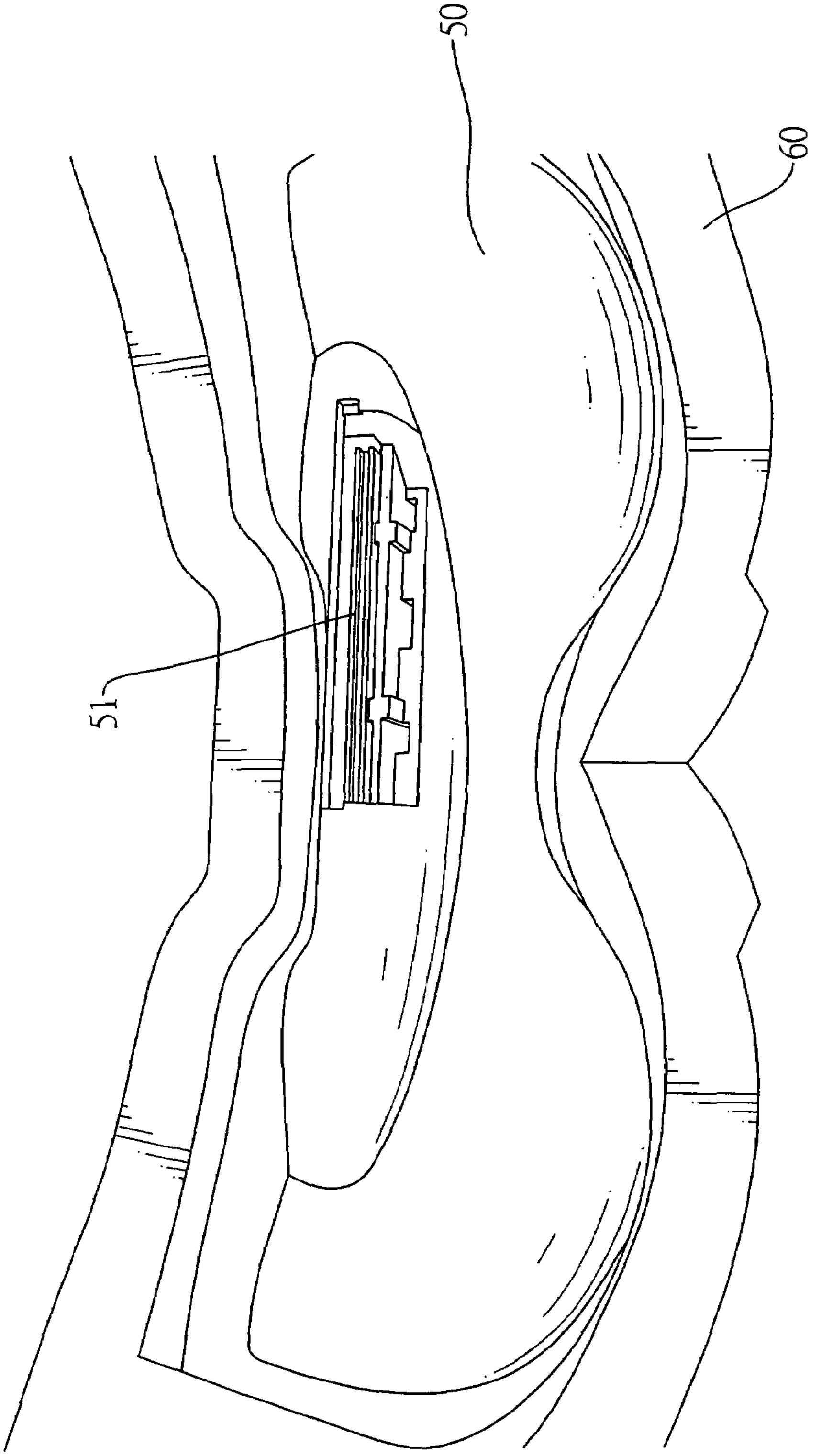
FIG. 6 is a rear perspective view of the eye muscle trainer.

The eye frame (50) fits the user's face, has a rear rim, accommodates the rear opening of the outer casing (10) and is semiopaque to allow only the lights generated from the light emitting units passing through the eye frame (50). With further reference to FIG. 6, the eye frame (50) further has a battery chamber (51) with a cover (52) to hold at least one battery (53) that provides electric power to the control circuit module (20).

The rim pad (60) is attached to the rear rim of the eye frame (50) to prevent ambient lights from interfering the lights emitted from the light emitting units and make the users feel more comfortable when wearing the eye muscle trainer.

The head belt (70) is held by the outer casing (10) and the eye frame (50) to assist the user in stably wearing the eye muscle trainer. The head belt (70) may be an elastic belt and may further have a length adjustment buckle (71) to allow the user adjust length of the head belt (70).

Based on the foregoing description, watching the light emitting units arranged at different position exercises the user's muscles around eyes. Therefore, wearing the eye muscle trainer of the present invention releases eyestrain. Furthermore, appropriate releasing eyestrain assists recovering eyesight.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. An eye muscle trainer comprising:

an outer casing being opaque and having a rear opening;

a control circuit module mounted in the outer casing and comprising two wing segments; and a center segment connected between the two wing segments of the control circuit module;

a first light emitting unit set mounted on the center of the center segment of the control circuit module for focusing a user's vision;

a second light emitting unit set mounted on the center segment of the control circuit module around the first light emitting unit set for focusing the user's vision on seeing straightly; and a third light emitting unit set mounted on the wing segments of the control circuit module for focusing the user's vision on seeing outwardly;

an eye frame accommodating the rear opening of the outer casing and allowing only light emitted from the light emitting units to pass through the eye frame.

2. The eye muscle trainer as claimed in claim 1, wherein a distance between the user's eyes and the light emitting unit sets when the user wears the eye muscle trainer is between 5 to 10 centimeters.

3. The eye muscle trainer as claimed in claim 1 further comprising a rim pad, wherein:

the eye frame has a rear rim and the rim pad is attached to the rear rim of the eye frame.

4. The eye muscle trainer as claimed in claim 1 further comprising a head belt held by the outer casing and the eye frame.

5. The eye muscle trainer as claimed in claim 4, wherein the head belt is an elastic belt.

6. The eye muscle trainer as claimed in claim 4, wherein the head belt further has a length adjustment buckle.

7. The eye muscle trainer as claimed in claim 1 further comprising a switch unit mounted in the outer casing and electrically connected to the control circuit module.

8. The eye muscle trainer as claimed in claim 1, wherein the eye frame further has a battery chamber with a cover to hold at least one battery that provides electric power to the control circuit module.

9. The eye muscle trainer as claimed in claim 1, wherein the second light emitting unit set comprises two light emitting units arranged horizontally on the center segment of the control circuit module and separated from each other by the first light emitting unit set.

* * * * *